US008217058B2

(12) United States Patent
Patel et al.

(10) Patent No.: US 8,217,058 B2
(45) Date of Patent: Jul. 10, 2012

(54) SUBSTITUTED PIPERIDINO PHENYLOXAZOLIDINONES

(75) Inventors: Mahesh Vithalbhai Patel, Aurangabad (IN); Mahesh Phansalkar, Panvel (IN); Vijaykumar Jagdishwar Patil, Solapur (IN); Milind Dattatraya Sindkhedkar, Pune (IN); Prasad Keshav Deshpande, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 494 days.

(21) Appl. No.: 12/225,744

(22) PCT Filed: May 8, 2007

(86) PCT No.: PCT/IB2007/001179
§ 371 (c)(1),
(2), (4) Date: Jul. 24, 2009

(87) PCT Pub. No.: WO2007/132314
PCT Pub. Date: Nov. 22, 2007

(65) Prior Publication Data
US 2010/0056581 A1    Mar. 4, 2010

(30) Foreign Application Priority Data
May 9, 2006 (IN) .......................... 719/MUM/2006

(51) Int. Cl.
*A61K 31/445* (2006.01)
*C07D 413/10* (2006.01)

(52) U.S. Cl. ........................................ 514/326; 546/209

(58) Field of Classification Search ................... 514/326; 546/209
See application file for complete search history.

(56) References Cited

U.S. PATENT DOCUMENTS

| 5,668,286 | A  | * | 9/1997 | Yamada et al. | ............... 546/209 |
| 7,687,627 | B2 | * | 3/2010 | Deshpande et al. | ............. 546/19 |
| 2009/0018123 | A1 | * | 1/2009 | Sindkhedkar et al. | ..... 514/227.8 |
| 2010/0056581 | A1 | * | 3/2010 | Patel et al. | ..................... 514/340 |
| 2010/0144735 | A1 | * | 6/2010 | Deshpande et al. | ....... 514/236.8 |

OTHER PUBLICATIONS

Larsen et al. "Drug Design and Discovery" p. 426 (2002).*
Wakefield "Fluorinated pharmaceuticals" Innovations in Pharmaceutical Technology v. 74, p. 76-78 (2003).*
Braga et al. "making crystal . . . " Roy. Soc. Chem. Chemm Commun. p. 3635-3645 (2005).*
Wolff "Burger's Medicinal Chem . . . " p. 975-977 (1995).*
Seddon "Psudopolymor . . . " Crystal growh & design, p. 1087 (2004).*
Jordan "Tamoxifen . . . " Nature Rev. 205-213 (2003).*
Vippagunta et al. "Crystalline solids . . . " Adv. DRug Del. Rev. v.48, p. 3-26 (2001).*

* cited by examiner

*Primary Examiner* — Celia Chang
(74) *Attorney, Agent, or Firm* — Bio Intellectual Property Serives LLC; O. M. (Sam) Zaghmout

(57) ABSTRACT

The present invention relates to certain substituted piperidino phenyloxazolidinones. Specifically, the invention relates to geminally disubstituted piperidino phenyloxazolidinones having antimicrobial activity with improved pharmacokinetic profile. The invention also relates to processes for the preparation of compounds of the present invention, pharmaceutical compositions containing the compounds of the present invention and the methods for treating or preventing microbial infections using the compounds of the present invention.

13 Claims, No Drawings

SUBSTITUTED PIPERIDINO PHENYLOXAZOLIDINONES

FIELD OF THE INVENTION

The present invention relates to certain substituted piperidino phenyloxazolidinones. Specifically, the invention relates to geminally disubstituted piperidino phenyloxazolidinones having antimicrobial activity with improved pharmacokinetic profile. The invention also relates to processes for the preparation of compounds of the present invention, pharmaceutical compositions containing the compounds of the present invention and the methods for treating or preventing microbial infections using the compounds of the present invention.

BACKGROUND OF THE INVENTION

Oxazolidinones represent a novel chemical class of synthetic antimicrobial agents. Linezolid represents the first member of this class to be used clinically. Oxazolidinones display activity against important Gram-positive human and veterinary pathogens including Methicillin-Resistant *Staphylococcus aureus* (MRSA), Vancomycin Resistant Enterococci (VRE) and β-lactam Resistant *Streptococcus pneumoniae* (PRSP). The oxazolidinones also show activity against Gram-negative aerobic bacteria, Gram-positive and Gram-negative anaerobes. (Diekema D J et al., *Lancet* 2001; 358: 1975-82).

Limitations of oxazolidinones have also surfaced. They are inactive against Enterobacteriaceae (Zhanel, G G et al., Canadian Journal of Infectious Diseases, 2001, 12:379-390). Moreover, their potency for atypical respiratory pathogens such as *Mycoplasma pneumoniae, M. hominis, Ureaplasma urealyticium* and *Chlamydia* species is of a borderline range which could result in unacceptable clinical efficacy for the treatment of respiratory tract infections (Diekema D. J. et al. *Lancet* 2001; 358:1975-82).

Other limitations, that have appeared through the clinical development studies and use of linezolid and its potential successors in development, are that this class of compounds have a propensity to induce myelosuppression with consequent thrombocytopenia (Kuter D J et al., *Pharmacotherapy*, 2001: 21: 1010-1030).

Inhibition of monoamine oxidase by oxazolidinones has prompted clinical use of the members of this class with concomitant usage of adrenergic or serotonergic agents and selective serotonin reuptake inhibitors (Ament P W et al., *Am Fam Physician* 2002, 65: 663-70). Furthermore, due to short half-life, linezolid has b.i.d dosing regimen.

There are several references disclosing antibacterial activity of oxazolidinones. For example, International (PCT) publication WO 95/25106 discloses substituted piperidino phenyloxazolidinones. International (PCT) publication WO 96/13502 discloses phenyloxazolidinones having a multisubstituted azetidinyl or pyrrolidinyl moiety. U.S. Patent application 04/0063954, International (PCT) publications WO 04/007489 and WO 2004/007488 disclose piperidinyl phenyl oxazolidinones for antimicrobial use. Pyrrodinyl/piperidinyl phenyl oxazolidinone antibacterial agents are also described in Kim H Y et al., *Bioorg. & Med. Chem. Lett.*, (2003), 13:2227-2230. International (PCT) publication WO 96/35691 discloses spirocyclic and bicyclic diazinyl and carbazinyl oxazolidinone derivatives where one of the hetero atoms in the ring is nitrogen. Diazepeno phenyloxazolidinone derivatives are disclosed in the International (PCT) publication WO 99/24428. International (PCT) publication WO 02/06278 discloses substituted aminopiperidino phenyloxazolidinone derivatives.

International (PCT) publications WO 04/007488 and WO 04/007489 disclose a novel series of oxazolidinones, which show increased potency, having bactericidal activity, in contrast to the earlier-described bacteriostatic activity of linezolid and literature described oxazolidinones. Unusual bactericidal activity is shown to be displayed not just against linezolid-sensitive strains but also for the first time against linezolid-resistant strains, thus indicating a differential binding at conventional site/s of the ribonucleoprotein and/or targeting multiple such receptor sites. International (PCT) publication WO 05/054234 discloses geminally disubstituted piperidine phenyloxazolidinones derivatives having improved in vivo efficacy.

The compounds, of the present invention have improved therapeutically favorable pharmacokinetic profile amenable for the development of once a day dosing oxazolidinone. The compounds of the invention thus establish their ability to give in vivo protection to animals and be useful clinically.

SUMMARY OF THE INVENTION

In one aspect there are provided novel piperidino substituted phenyloxazolidinone compounds of Formula-I:

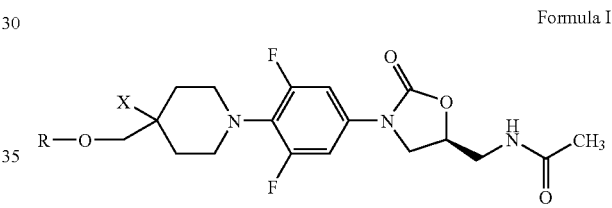

Formula I and their pharmaceutically acceptable salts, pharmaceutically acceptable solvates, esters, polymorphs, enantiomers, or diastereomers, wherein X is OH or F; and R is $CH_3$, —$(CH_2)_n$—$CF_3$, —$(CH_2)_n$—$CHF_2$, wherein n is 0, 1 or 2.

In another aspect, pharmaceutical compositions containing such compounds are provided together with pharmaceutically acceptable carriers, excipients or diluents which can be useful for treating or preventing microbial infections.

The enantiomers, diasteromers, polymorphs, pharmaceutically acceptable salts and pharmaceutically acceptable solvates of these compounds as well as metabolites having the same type of activity are also provided, as well as pharmaceutical compositions comprising the compounds, their metabolites, enantiomers, diastereomers, polymorphs, solvates or pharmaceutically acceptable salts thereof, in combination with a pharmaceutically acceptable carrier and optionally included excipients.

Other aspects will be set forth in the description which follows, and in part will be apparent from the description or may be learnt by the practice of the invention.

DETAILED DESCRIPTION OF THE INVENTION

In one aspect, there are provided compounds having the structure of Formula I:

Formula I

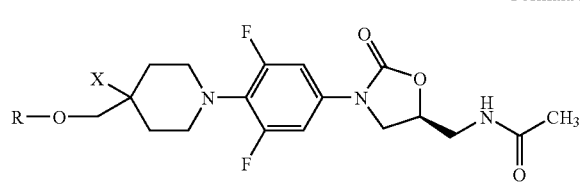

and their pharmaceutically acceptable salts, pharmaceutically acceptable solvates, esters, polymorphs, enantiomers, or diastereomers, wherein
X is OH or F; and
R is $CH_3$, $-(CH_2)_n-CF_3$, $-(CH_2)_n-CHF_2$, wherein n is 0, 1 or 2.

Specific compounds of the invention are:
(5S)—N-{3-[3,5-difluoro-4-(4-hydroxy-(4-methoxymethyl)-piperidin-1yl)phenyl]-2-oxo-oxazolidin-5-ylmethyl}-acetamide;
(5S)—N-{3-[3,5-difluoro-4-(4-fluoro-(4-methoxymethyl)-piperidin-1yl)phenyl]-2-oxo-oxazolidin-5-ylmethyl}-acetamide;
(5S)—N-{3-[3,5-difluoro-4-(4-hydroxy-4-(2,2,2-trifluoroethoxymethyl)-piperidin-1-yl)-phenyl]-2-oxo-oxazolidin-5-ylmethyl}-acetamide.

The compounds of the invention have shown significantly better pharmacokinetic advantage suitable for once a day dosing. For example, the compound (5S)—N-{3-[3,5-difluoro-4-(4-hydroxy-(4-methoxymethyl)-piperidin-1yl)phenyl]-2-oxo-oxazolidin-5-ylmethyl}-acetamide of the invention shows significantly higher serum concentrations above the MIC value up to 24 h post dosing, in dog pharmacokinetic study. Thus, indicating once a day potential of the compounds of the invention.

In another aspect, there are provided processes for preparing the compounds of Formula I. The starting-materials may be prepared by any of the methods known in the art including those described in U.S. Pat. No. 5,668,286; US Publication Nos. 2004/0063954 and 2005/0143421 or by procedures that would be well known to one of ordinary skill in the art of synthetic organic chemistry.

The following abbreviation are used in the text: DCM for dichloromethane, DMAP for 4-dimethylaminopyridine, DMF for N,N-dimethylformamide, DMSO for dimethyl sulfoxide, EtOAc for ethyl acetate, TEA for triethylamine, THF for tetrahydrofuran, $Ac_2O$ for acetic anhydride, PPTS for pyridinium para-toluenesulfonate, PTSA for para-toluene sulfonic acid, LDA for lithium diisopropylamine, DMAc for dimethyl acetamide.

The compound 4, which is the starting material for the preparation of compounds of Formula I may be prepared by the reaction sequence as generally shown in Scheme 1.

Scheme-1

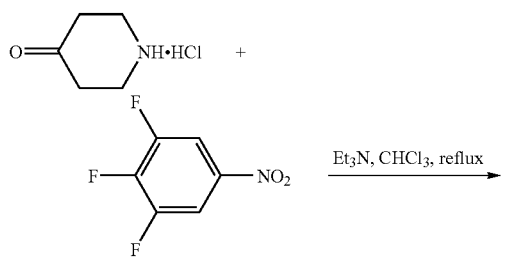

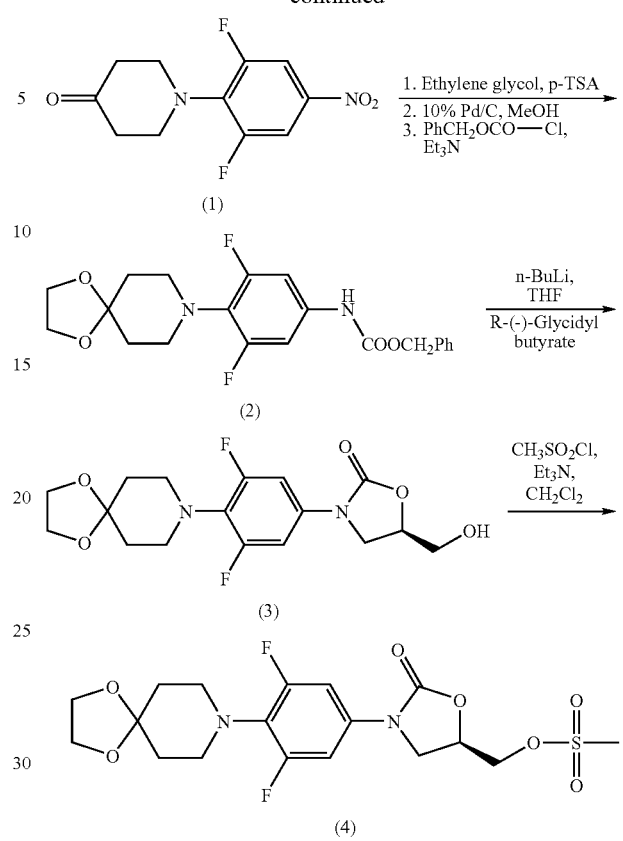

As shown in Scheme-1,4-piperidone hydrochloride can be condensed with 3,4,5-trifluoro-nitrobenzene in the presence of a base such as triethylamine to give compound (1). The compound (1) can be treated with ethylene glycol to protect the carbonyl group. The nitro group in this compound can be reduced with a catalytic amount of 10% Pd/C in the presence of ammonium formate or iron in the presence of ammonium chloride to obtain the corresponding amino compound. The amino compound can be further treated with benzyl chloroformate to give compound (2). The compound (2) can be treated with R-(-)-glycidyl butyrate in the presence of a base such as n-butyl lithium, lithium diisopropylamine, lithium hexamethyldisilazane to give compound (3). The compound (3) can be treated with methanesulphonyl chloride in the presence of a base such as triethylamine to give the compound (4).

The compounds of Formula I can be prepared from the compound (4) using the following steps:
a) converting compound (4) into compound of Formula II;

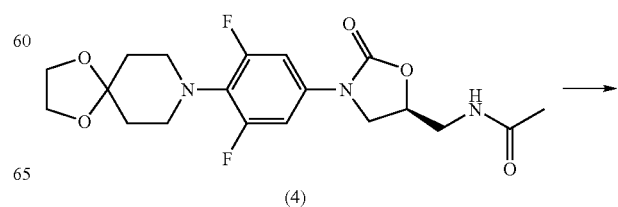

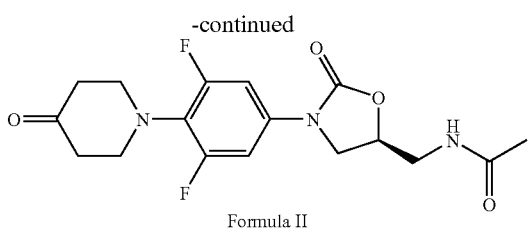

Formula II b) converting carbonyl of compound of Formula II into epoxide to form a compound of Formula III using a suitable reagent; and Formula III

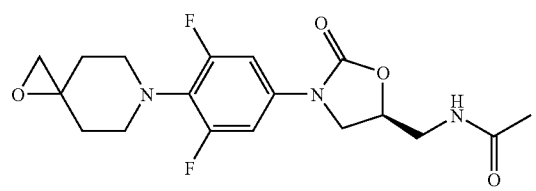

c) opening the epoxide of compound of Formula III to give a compound of Formula I(a) or Formula I(b).

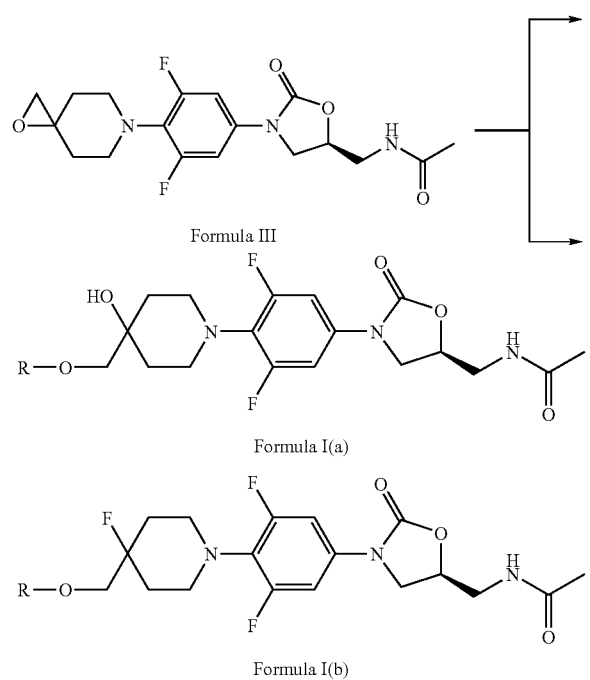

The compound of Formula I(a) may be converted into compound of Formula I(b) using a fluorinating reagent.

The compound (4) can be converted to the compounds of invention of Formula II by the reaction sequences as generally shown in Scheme-2 and Scheme-3. The synthesis involves transformations at C-5 of the oxazolidinone moiety and at the C-4 of the piperidine moiety. The sequence of transformation can be carried out in any suitable order as would be known to one skilled in the art of organic chemistry. In general, the steps may comprise:

a) hydrolyzing the ketal group to convert into carbonyl group;
b) converting mesylate group to azide;
c) reducing the azide to amine;
d) acetylating the amine to form acetamide.

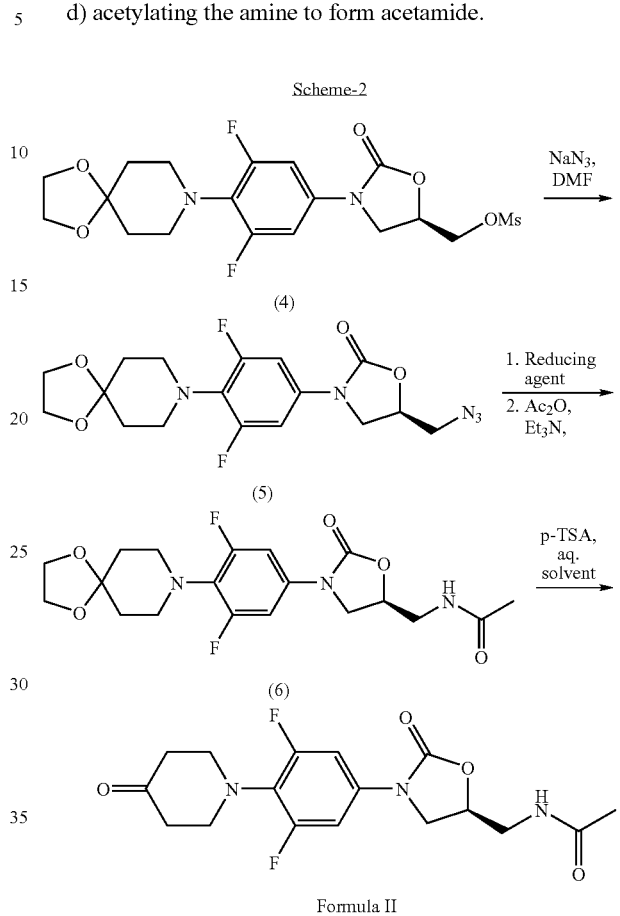

As shown in Scheme-2, the compound (4) can be converted into azido compound (5) by treating compound (4) with sodium azide in a solvent such as DMF or aqueous DMF or DMAc at a temperature between 30 to 100° C. for 1 to 48 hours. The azido compound (5) can be reduced to amino group upon treatment with a catalyst such as 5% palladium on carbon, 10% palladium on carbon, 20% palladium hydroxide on carbon, platinum on carbon or Raney-Nickel in the presence of a hydrogen source such as hydrogen gas, ammonium formate or cyclohexene in a solvent such as methanol, ethanol, ethyl acetate, tetrahydrofuran, or a mixture thereof at a temperature between 0-80° C. for 1 to 12 hours to provide the corresponding amino compound. Alternately, the azido compound can be reduced to amino compound by using the reagent sodium borohydride-cobalt chloride in a solvent such as tetrahydrofuran or by treating with triphenyl phospine followed by water in a suitable solvent and isolating the free amine. The amino compound can be further treated with acetic anhydride in the presence of a base such as triethylamine or pyridine in an organic solvent such as chloroform, dichloromethane, ethyl acetate to give the corresponding acetamido compound (6). The compound (6) can be treated with para-toluene sulphonic acid or pyridinium para-toluenesulfonate (PPTS) in an aqueous solvent such as aqueous acetone or acetonitrile to give compound of Formula II.

Alternately, as shown in Scheme-3, the compound (4) can be treated with para-toluene sulphonic acid or PPTS in an aqueous organic solvent such as acetone at 70° C. to give compound (7). The mesylate group can be converted to azide group by treating compound (7) with sodium azide in a solvent such as DMF or aqueous DMF at a temperature between 30 to 100° C. for 1 to 48 hours to give compound (8). The azido compound (8) can be reduced to amino upon treatment with a catalyst such as 5% palladium on carbon, 10% palladium on carbon, 20% palladium hydroxide on carbon, platinum on carbon or Raney-Nickel in the presence of a hydrogen source such as hydrogen gas, ammonium formate or cyclohexene in a solvent such as methanol, ethanol, ethyl acetate, tetrahydrofuran, or a mixture thereof at a temperature between 0-80° C. for 1 to 12 hours to provide the corresponding amino compound. The amino compound can be further treated with acetic anhydride in the presence of a base such as triethylamine or pyridine in a halogenated solvent such as chloroform, dichloromethane to give the compound of Formula II.

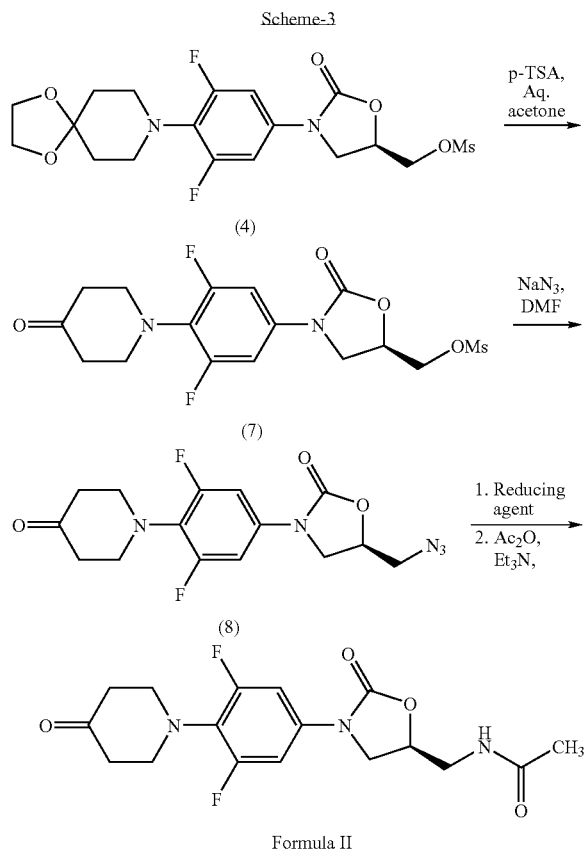

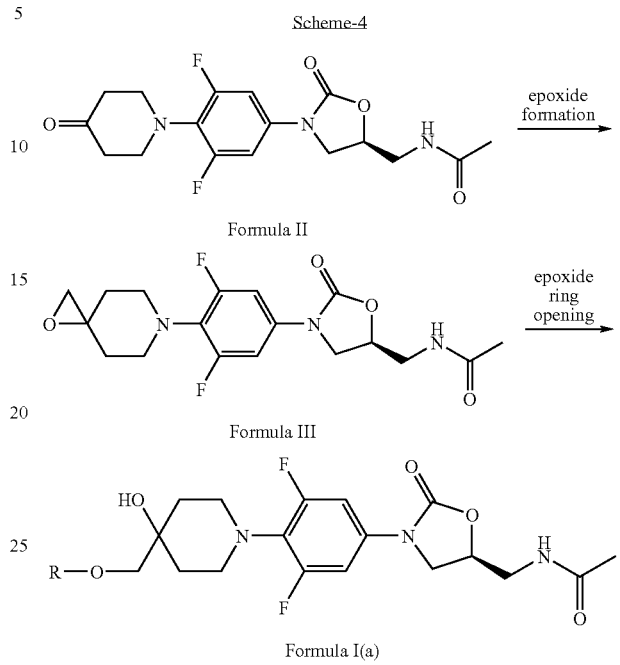

Compounds of Formula I(a) can be prepared by the reaction sequence as shown in Scheme-4. The compound of Formula II can be converted into epoxide of Formula III using a suitable reagent in the presence of a base. The reaction can be carried out using trimethyloxosulfonium iodide or trimethyloxosulfonium chloride in the presence of a base such as sodium hydride, potassium tert-butoxide, LDA, or n-butyl lithium in a solvent such as DMSO, DMF, THF, or a mixture thereof at a temperature between 0-85° C. for 1 to 12 hours to provide epoxide containing compound of Formula III.

The compound of Formula III, when treated with a suitable reagent like an alkoxide such as sodium methoxide or a base such as sodium carbonate, potassium carbonate, sodium tert-butoxide or potassium tert-butoxide in an alcoholic solvent such as methanol, trifluoromethanol, difluoroethanol, trifluoroethanol, difluoropropanol or trifluoropropanol yields the compound of invention of Formula I(a)

As shown in Scheme-5, the compound of Formula I(b) can be prepared by treating compound of Formula I(a) with a fluorinating agents such as diethylaminosulfur trifluoride (DAST), dimethylaminosulfur trifluoride, pyrrolidino sulfur trifluoride, N,N-diethyl-1,1,2,3,3,3-hexafluoro propyl amine, N,N-diethyl-1,2,3,3,3-pentafluoro propenamine, hydrogen fluoride or tetra butyl ammonium fluoride in an organic solvent such as dichloromethane, chloroform and stirred for 1 to 24 h at a temperature between −20 to 50° C.

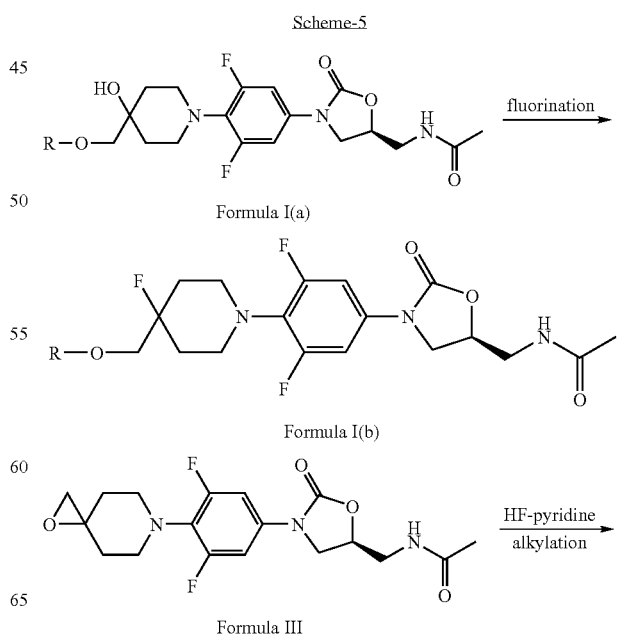

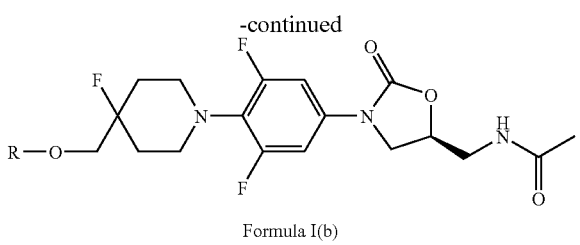

Formula I(b)

Alternately, for the preparation of compounds of Formula I(b), the compound of Formula III can be treated with 70% HF-pyridine in a solvent such as dichloromethane, chloroform at a temperature between −40 to +60° C. to give the corresponding fluoro derivative as shown in Scheme-5. The product can be further alkylated using the standard alkylation methods known in the art of organic chemistry to give the compound of Formula I(b), for example when R is $CH_3$, typically the alkylation can be performed using methyl iodide in the presence of silver oxide.

The oxazolidinone antimicrobial agents of present invention have potential for treatment of especially Gram-positive infections including multi-resistant strains. In contrast to the compounds of the prior art, they demonstrate bactericidal activity against different resistant microorganisms and in particular different strains of *Enterococcus faecalis*. In addition, they display activity against linezolid-resistant *S. aureus* strains, linezolid-resistant *E. faecalis* strains and in particular linezolid-resistant *S. pneumoniae* strains. These compounds are useful for the treatment of Gram-positive, Gram-negative bacteria, aerobic, anaerobic bacteria or atypical bacterial infections in humans and other warm-blooded animals by parenteral, oral or topical administration. The infection in human and other warm-blooded animals can be systemic or topical.

Examples of infections that may be treated with the compounds of the present invention include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. Specifically, infectious diseases that may be treated with the compounds of the present invention are gram-positive infections such as osteomyelitis, endocarditis and diabetic foot.

The compounds described herein are useful for the treatment or prophylaxis of Gram-positive or Gram-negative bacteria, aerobic, anaerobic bacteria or atypical bacterial infections in humans and other warm-blooded animals. The oxazolidinone antimicrobial compounds of present invention are useful for treatment of Gram-positive infections including those, which result from multi-resistant strains. The compounds of present invention are useful antimicrobial agents effective against various humans and veterinary pathogens specially included Linezolid-resistant strains.

In contrast to linezolid, the compounds described herein demonstrate bactericidal activity against different resistant microorganisms and in particular different strains of *Enterococcus faecalis*. In addition they display activity against linezolid-resistant *S. aureus* strains, linezolid-resistant *E. faecalis* strains and in particular linezolid-resistant *S. pneumoniae* strains.

The infection in human and other warm-blooded animals can be systemic or topical. The compounds of present invention may be used to prevent infections caused by Gram-positive and Gram-negative bacteria, aerobic, anaerobic bacteria or atypical bacteria by administering the compound to a subject that is at risk for developing an infection caused by bacteria. A subject at risk for developing an infection may be a health care worker, surgical patient, immune-comprised or the like.

The present invention encompasses certain compounds, compositions, dosage forms, and methods of administering the compounds to a human or other animal subject. In an embodiment of the invention, the pharmaceutical compositions contain an therapeutically effective amount of the active compounds of the invention, its derivatives, prodrugs, salts or hydrates thereof described in this specification in admixture with a pharmaceutically acceptable carrier, diluent or excipients, and optionally other therapeutic ingredients. Specific compounds, compositions and dosage forms to be administered must, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. The pharmaceutical compositions are prepared according to conventional procedures used by persons skilled in the art to make stable and effective compositions. In the dosage forms, a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effect dose level for any particular patient will depend upon a variety of factors including the disorder being treated with the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

For the purpose of present invention, a pharmaceutical composition may contain one or more of the active compounds of the invention, their derivatives, salts, prodrugs and/or hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

The compounds and compositions can be administered to a human or other animal by any suitable route of administration including, for example, oral, rectal, vaginal, parenteral, (subcutaneous, intramuscular, intravenous), transdermal, topical and like. Dosage forms include solutions, suspensions, tablets, pills, powders, troches, dispersions, suspensions, emulsions, solutions, pellets, gels, granules, capsules, injectable preparations, patches, ointments, creams, liniments, salves, cachets, aerosol sprays, lotions, shampoos and the like.

The prophylactic or therapeutic dose of the compounds of the invention, their derivatives, salts, prodrugs or hydrates thereof, in the prevention, acute or chronic management of infection or disease will vary depending on one or more factors which include but are not limited to the severity of condition to be treated, the risk and the route of administration. In addition, the dose, and perhaps the dose frequency, will also vary according to the age, sex, body weight and response of the individual patient. In general, the total daily dose range, for the compounds of the invention, the derivatives, salts, prodrugs or hydrates thereof, for the conditions described herein, is from about 200 mg to about 1500 mg, in single or divided doses. In a non-limiting embodiment, a daily dose range should be between about 400 mg to 1200 mg, in single or divided dosage, while most preferably a daily dose range should be between about 500 mg to about 1000 mg in divided dosage. While parenteral administration may be a single dose or up to 3 divided doses, intravenous administration can include a continuous drip.

It may be necessary to use dosages outside these ranges in some cases as will be apparent to those skilled in the art. Further, it is noted that the clinician or treating practitioner will know how and when to interrupt, adjust, or terminate therapy in conjunction with individual patient's response or condition or whether the infection is active or the treatment is prophylactic. The term "an amount sufficient to eradicate such infections but insufficient to cause undue side effects" is encompassed by the above-described dosage amount and dose frequency schedule.

A specific embodiment of the invention is that the pharmacokinetic profile of a compound of the invention is such that it permits administration of a once-a-day dosing.

Pharmaceutical compositions of the present invention suitable for oral administration may be presented as discrete units, for example, such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general below are commonly used in the case of oral solid preparations (such as powders, capsules and tablets), with the oral solid preparations being preferred over the oral liquid preparations. The most preferred oral solid preparation is tablets and capsules.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques. In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

Desirably, each oral dosage form contains from about 200 mg to about 1500 mg of the active ingredient. Most preferably, the tablet, cachet or capsule contains either one of three dosages, about 200 mg, about 400 mg, or about 600 mg of the active ingredient.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration in which case parenteral dosages are employed. Parenteral dosages employed may be in the form of ready to use dosage forms or solutions for parenteral dosage may be diluted prior to its use.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

A third preferred route of administration is topically, for which creams, ointments, shampoos, lotions, dusting powders and the like are well suited. Generally, an effective amount of the compound according to present invention in a topical form is from about 0.1% w/w to about 10% w/w of the total composition. Preferably, the effective amount of the compound of the invention is 1% w/w of the total composition.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

A non-limiting embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful. The antimicrobial pharmaceutical composition may further contain ordinary dissolving aids, buffers, pain-alleviating agents, and preservatives, and optionally coloring agents, perfumes, flavors, sweeteners, and other drugs.

An advantage of present invention is that compounds have favorable safety advantages as compared to linezolid, in particular compounds of the present invention do not cause or lower the potential to cause myelosuppression. Myelosuppression is known to be a typical class-specific toxicological feature of the oxazolidinone class of antimicrobial agents.

While the present invention has been described in terms of its specific embodiments, certain modifications and equivalents will be apparent to those skilled in the art and are included within the scope of the present invention. Following examples illustrate the methods of preparation of the compounds of the invention and are provided only as examples, but not to limit the scope of the compounds of the present invention.

Example-1

1-(2,6-Difluoro-4-nitrophenyl)-piperidin-4-one

To a mixture of 3,4,5-trifluoronitrobenzene (3.894 g, 0.022 mol) and 4-piperidone hydrochloride monohydrate (3.072 g, 0.020 mol) in chloroform (24 ml), was added triethylamine (8.3 ml, 0.06 mol) under stirring. The resulting mixture was heated and stirred at 70° C. for 7 h. After completion of the reaction (TLC), the solvent was evaporated under reduced pressure and the residue diluted with water (10 ml). The separated solid was filtered, washed with water (8 ml) followed by hexane (5 ml) to obtain yellow crystalline solid as a product, 4.8 g, 94% yield M.P.: 130-132° C.; MS: M+1=257 (MH+ 100%) for M.F.: $C_{11}H_{10}F_2N_2O_3$ Example-2

[4-(1,4-Dioxa-8-aza-spiro[4.5]dec-8-yl)-3,5-difluoro-phenyl]-carbamic acid benzyl ester To a mixture of compound of example-1 (5.632 g, 0.022 mol) in toluene (40 ml), ethylene glycol (2.48 g, 0.040 mol) and p-toluenesulfonic acid monohydrate (0.988 g, 0.0052 mol) were added under stirring. The reaction mixture was heated at 110-120° C. and water was removed azeotropically. After completion of the reaction, the contents were neutralized with sodium bicarbonate solution (~12 ml). The layers were separated and the toluene layer was taken in a round bottom flask. Pd/C (10%, 1 g) was added to the toluene layer and the contents were stirred for 24 h under $H_2$ atmosphere. After completion of the reaction, the catalyst was filtered and washed with chloroform (10 ml). The filtrate was charged into a round bottom flask and sodium bicarbonate (5.04 g, 0.06 mol) was charged to get a suspension. Benzylchloroformate (50% solution in toluene, 9 ml, 0.026 mol) was added over a period of 10 min. to the suspension under stirring. The reaction mixture was stirred for additional 1 h. After completion of the reaction, the solids were filtered and washed with chloroform (10 ml). The filtrate was concentrated under vacuum and hexane (10 ml) was added to obtain a solid product. The solid was filtered and dried under vacuum at 70-80° C. to obtain an off white product, 7.2 g, 81% yield.
M.P.: 126-128° C.; MS: M+1=405 (MH+ 100%); for M.F.: $C_{21}H_{22}F_2N_2O_4$ Example-3

5(R)-3-[4-(1,4-Dioxa-8-azaspiro[4.5]dec-8-yl)-3,5-difluorophenyl]-5-(hydroxymethyl)-1,3-oxazolidin-2-one To a mixture of a compound of example-2 (7.19 g, 0.0178 mol) in dry tetrahydrofuran (THF) (45 ml) at 40° C., n-BuLi in hexane (1.6 M, 13.1 ml, 0.021 mol) was charged over a period of 10 min under nitrogen atmosphere. The contents were stirred for further 1 h at 40° C. and R-(–)-glycidyl butyrate (2.6 g, 0.018 mol) was added gradually over a period of 15 min. The reaction mixture was stirred for 1 h and after completion of the reaction, methanol (4.75 ml), sodium methoxide (0.15 g, 0.0028 mol) and water (0.5 ml) were added to the flask. The contents were stirred for additional 0.5 h and saturated solution of ammonium chloride (20 ml) was added to it. The contents were extracted with ethyl acetate (2×20 ml) and the organic layer was evaporated under vacuum to obtain a thick residue. Toluene (12 ml) was added to the residue to obtain a solid product, which was filtered and washed with toluene (4 ml). The residue was dried under reduced pressure at 50-60° C. to obtain the product as an off-white solid, 3.5 g, 53% yield.
M.P.: 152-154° C.; MS: M+1=371, (MH+ 100%) for M.F.: $C_{17}H_{20}F_2N_2O_5$.

Example-4

(5R)-{3-[4-(1,4-Dioxa-8-azaspiro[4.5]dec-8-yl)-3,5-difluorophenyl]-2-oxo-oxazolidin-5-ylmethyl}-methanesulfonate To a mixture of compound of example-3 (3.44 g, 0.0093 mol) in dichloromethane (23 ml), triethylamine (2.5 ml, 0.018 mol) was added under stirring. Methanesulfonyl chloride (1.385 g, 0.0121 mol) was added over 10 min to the solution at room temperature and the reaction mixture was stirred for further 2 h. After completion of the reaction, the contents were evaporated under vacuum at 40° C. to obtain an oily residue. Water (10 ml) was added to the residue and the traces of dichloromethane were removed under vacuum. The residue was washed with additional water (5 ml) and dried under reduced pressure at 70° C. to obtain the product as a white solid, 3.95 g, 95% yield.
M.P.: 144-146° C.; MS: M+1=449 (MH+ 100%) for M.F.: $C_{18}H_{22}F_2N_2O_7S$.

Example-5

(5R)-3-[4-(1,4-Dioxa-8-azaspiro[4.5]dec-8-yl)-3,5-difluorophenyl]-5-(azidomethyl)-oxazolidin-2-one To a solution of compound of example-4 (4.166 g, 0.0093 mol) in N,N-dimethylformamide (8 ml), sodium azide (1.82 g, 0.028 mol) was added under stirring. The reaction mixture was heated gradually and the temperature was maintained at 70° C. for 8 h. After completion of the reaction, the contents were cooled to 20-25° C. and poured slowly in chilled water (50 ml). The solid product thus obtained was filtered and washed with water (10 ml) and dried at RT to obtain the product as a off-white solid, 3.48 g, 96% yield.

M.P.=Not checked being an azide; MS: M+1=396 (MH$^+$ 100%) for M.F.: $C_{17}H_{19}F_2N_5O_4$ Example-6

(5S)—N-{3-[4-(1,4-dioxa-8-azaspiro[4.5]dec-8-yl)-3,5-fluorophenyl]-oxazolidin-2-oxo-oxazolidin-5-ylmethyl}-acetamide To a solution of compound of example-5 (3.673 g, 0.0093 mol) in THF (23 ml), sodium borohydride (1.21 g, 0.032 mol) and cobalt chloride (0.547 g, 0.0023 mol) were charged over a period of 30 min. The reaction mixture was stirred at room temperature for 2 h. After completion of the reaction, the contents were filtered through a filter-aid bed and the bed was washed with THF (5 ml). The filtrates were combined and concentrated under vacuum at 60-70° C. to obtain an oily product. Ethyl acetate (20 ml) was added to the oily product to get a clear solution and it was filtered through a filter-aid bed and the bed was washed with ethyl acetate (5 ml). The combined filtrates were washed with water (20 ml) and the organic layer was dried over sodium sulfate. Triethylamine (3.2 ml, 0.023 mol) was added to the above organic layer and acetic anhydride (1.7 g, 0.0166 mol) was added gradually over a period of 15 min at room temp. The reaction mixture was stirred for 2 h and after completion of the reaction; the contents were evaporated under vacuum to obtain a residue. Water (20 ml) was added to the residue and the traces of ethyl acetate were removed under the vacuum. The solid product thus obtained was filtered and washed with water (5 ml). The residue was dried at RT to obtain the product as a white solid, 2.29 g, 60% yield over two steps M.P.: 218-220° C.; MS: M+1=412 (MH$^+$ 100%); for M.F.: $C_{19}H_{23}F_2N_3O_5$.

Example-7

(5R)-{3-[3,5-Difluoro-4-(4-oxopiperidin-1-yl)phenyl]-2-oxo-oxazolidin-5-yl methyl}-methane-sulfonate The compound, example-4 (17 g, 0.035 mol) was charged into a mixture of water (100 ml) and acetone (200 ml) under stirring. p-Toluenesulfonic acid monohydrate (0.067 mol) was added to the stirring mixture and the contents were heated and maintained at 70° C. for 3.5 h. After completion of the reaction, the contents were cooled to 30° C. and neutralized to pH 7-7.5 with sodium bicarbonate. Acetone was removed under vacuum at 60-65° C. to obtain a thick mass. Water (25 ml) was added to the mass and the contents were cooled to 5-10° C. The solid product thus obtained was filtered, washed with water (10 ml) and dried under reduced pressure at 80-85° C., to obtain a white solid as a product, 14 g, 91% yield.

M.P.: 152° C. MS: M+1=405 (MH$^+$ 100%); for M.F.: $C_{16}H_{18}F_2N_2O_6S$.

Example-8

(5R)-{3-[3,5-Difluoro-4-(4-oxopiperidin-1-yl)phenyl]-5-(azidomethyl)-oxazolidin-2-one To a solution of example-7 (3.01 g, 0.0093 mol) in N,N-dimethylformamide (8 ml), sodium azide (1.82 g, 0.028 mol) was charged under stirring. The reaction mixture was heated gradually and the temperature was maintained at 70° C. for 8 h. After completion of the reaction, the contents were cooled to 20-25° C. and poured slowly in chilled water (50 ml). The solid product thus obtained was filtered and washed with water (10 ml) and the residue dried at room temperature to obtain the product as an off white solid. The wet product was used for next reaction without drying.

MS: M+1=398, for M.F.: $C_{17}H_{21}F_2N_5O_4$.

Example-9

(5S)—N-{3-[3,5-Difluoro-4-(4-oxopiperidin-1-yl)phenyl]-2-oxo-oxazolidin-5-ylmethyl}-acetamide Method A: The example-6 (2.8 g, 0.0068 mol) was added to a mixture of water (34.5 ml) and acetone (23 ml) under stirring. p-Toluenesulfonic acid monohydrate (2.47 g, 0.013 mol) was added to the stirring mixture and the contents were heated and maintained at 70° C. for 3 h.

After completion of the reaction (TLC), the contents were cooled to 30-35° C. and neutralized to pH 7-7.5 with sodium bicarbonate (~1.2 g). The reaction mixture was concentrated under reduced pressure to obtain a thick mass Water (25 ml) was added to the mass and the contents were cooled to 5-10° C., the separated solid was filtered and the residue washed with additional water (10 ml). The residue was dried at 80-85° C. under reduced pressure to obtain the product as a white solid, 1.64 g, 66% yield.

M.P.: 132-134° C.; MS: M+1=368 (MH$^+$, 100%); for M.F.: $C_{17}H_{19}F_2N_3O_4$ Method B: A one lit. Parr reactor was charged with ethyl acetate 120 ml., pyridine (2.76 ml, 0.034 mol), example-8 (12 g, 0.034 mol) acetic anhydride (3.6 ml, 0.038 mol) and 1.2 g of 10% Pd/C (50% wet) and the mixture hydrogenated at 200 psi. After completion of reaction (4 h, as monitored by TLC), the reaction mixture was filtered through hyflow bed. The residue was washed with chloroform (50 ml). The combined filtrate was concentrated under reduced pressure. The residual semi solid was stirred with diethyl ether (50 ml), and the ethereal layer decanted. The residual solid was stirred with 50 ml distilled water for 30 min., The separated solid was filtered, washed with distilled water and dried under reduced pressure to obtain the product as white solid, 7.5 g, 82% yield.

M.P.: 132-134° C.; MS: M+1=368 (MH$^+$, 100%); for M.F.: $C_{17}H_{19}F_2N_3O_4$ Example-10

(5S)—N-{3-[4-(1-Oxa-6-azaspiro[2.5]oct-6-yl)-3,5-difluorophenyl]-2-oxo-oxazolidin-5-ylmethyl}-acetamide To a solution of trimethylsulfoxonium chloride (0.67 g, 0.0052 mol) in THF (13 ml) was added potassium tert-butoxide (0.617 g, 0.0055 mol) at RT and the contents were refluxed for 4-5 h. Example-7 (1.6 g, 0.0044 mol) was added in portions in 1 min to the refluxing mixture. The reaction mixture was further refluxed for 2 h. After completion of the reaction (TLC), the THF was evaporated under reduced pressure to obtain a thick residue. Water (20 ml) was added to the residue stirred well and the separated solid was filtered & washed with water (5 ml). The residue was dried under reduced pressure at 60-70° C. to obtain the product as a white solid, 1.57 g, 94% yield.

M. P.: 160-162° C.; MS: M+1=382 (MH+, 100%); for M. F: $C_{18}H_{21}F_2N_3O_4$

Example-11

(5S)—N-{3-[3,5-difluoro-4-(4-hydroxy-(4-methoxymethyl)-piperidin-1yl)phenyl]-2-oxo-oxazolidin-5-ylmethyl}-acetamide The example-10 (54.86 g, 0.144 mol) was suspended in methanol (1100 ml) under stirring at RT. Sodium metal (4 g, 0.174 mol) was added in small lots in 2 min to the above suspension under stirring. The reaction mixture was warmed to 40-42° C. and was stirred at this temperature for about 40 hrs. After completion of the reaction (TLC), the solvent was evaporated under reduced pressure to obtain a thick slurry. The thick slurry thus obtained was gradually added to water (1100 ml) under stirring. After the complete addition, the pH of the aqueous suspension was adjusted to 7 by adding sufficient quantity of glacial acetic acid. The separated solid was filtered and the residue was washed with water. The obtained solid was further purified by column chromatography over silica gel to obtain the product as a white solid, 32.7 g, 55% yield.

M.P.: 173-174° C.; MS: M+1=414 (MH+, 100%); for M.F.: $C_{19}H_{25}F_2N_3O_5$ $^1$H-NMR (400 MHz, CDCl$_3$): δ 7.0-7.1 (m, 2H, Ar—H), 6.0 (t, 1H, NH), 4.70-4.80 (m, 1H), 4.00 (t, 1H), 3.70-3.75 (m, 2H), 3.5-3.7 (m, 1H), 3.43 (s, 3H, OCH$_3$), 3.37-3.42 (m, 2H), 3.30 (s, 2H, —OCH$_2$), 3.0-3.05 (m, 2H), 2.22 (bs, 1H, —OH), 2.04 (s, 3H, COCH$_3$), 1.70-1.75 (m, 4H).

Example-12

(5S)—N-{3-[3,5-difluoro-4-(4-fluoro-(4-methoxymethyl)-piperidin-1yl)phenyl]-2-oxo-oxazolidin-5-ylmethyl}-acetamide To a solution of Example-11 (0.475 g, 1.15 mmol) in dichloromethane (10 ml) was added DAST (0.232 g, 1.44 mmol) and stirred for 8 h at 0° C. The solvent was evaporated and the residue purified by column chromatography to obtain the product as a white solid, 50 mg, in 10% yield.

MS: (M+1)=416; (MH+, 100%); M.F.: $C_{19}H_{24}F_3N_3O_4$

Example-13

(5S)—N-{3-[3,5-difluoro-4-(4-hydroxy-4-(2,2,2-trifluoro-ethoxymethyl)-piperidin-1-yl)-phenyl]-2-oxo-oxazolidin-5-ylmethyl}-acetamide To a solution of example-10 (2.75 mmol) in 2,2,2-trifluoroethanol (10 mL) was added K$_2$CO$_3$ (4.40 mmol) and the resulting mixture stirred at 25° C. for 18 h. The solvent was evaporated and the residue suspended in water (10 mL), stirred well and extracted with ethyl acetate (2×25 mL). The extract was concentrated and the residue purified on a column of silica gel to obtain the product as a white solid in 58% yield.

M.P. 182-184° C. and MS (M+1)=482.1 (MH+, 100%) for M.F.=$C_{20}H_{24}F_5N_3O_5$.

Biological Test Example-1

The in vitro MIC methods of test compounds were determined essentially as described in WO 95/25106, U.S. Pat. No. 5,668,286 and EP 0 750 618 B1.

MIC Test Method

Overnight grown cultures of MRSA-032 organisms in Tryptic Soya broth were diluted in Mueller Hinton Broth to give optical density matching with MacFarland tube 0.5 standard. Cultures were further diluted 1:10 in Mueller Hinton broth. Using Denley's multipoint inoculator, 10$^4$ cells were deposited on Mueller Hinton agar (Difco) containing range of 2 fold dilutions of test compounds. These plates were incubated for 24 h at 35° C. and MIC results recorded. MIC is defined as minimum drug concentration that inhibits test organisms. MIC results of the compound of invention is tabulated in Table-1.

TABLE 1

MIC of the Example-11

| Organism | MIC (mcg/ml) |
|---|---|
| Staphylococcus aureus ATCC 25923 | 2 |
| Staphylococcus aureus ATCC 29213 | 2 |
| Staphylococcus aureus Smith | 2 |
| Staphylococcus aureus STA-014 | 4 |
| Staphylococcus aureus MRSA-032 | 4 |
| Staphylococcus aureus Mu-50 VISA | 2 |
| Staphylococcus epidermidis STE-118 | 1 |
| Staphylococcus epidermidis STE-110 MRSE | 1 |
| Enterococcus faecalis ATCC 29212 | 2 |
| Enterococcus faecalis Efe-406 VRE | 4 |
| Enterococcus faecium Efa-303 | 4 |
| Enterococcus faecium Efa-332 VRE | 2 |
| Streptococcus pneumoniae ATCC 49619 | 2 |
| Streptococcus pneumoniae ATCC 6303 | 2 |
| Streptococcus pyogenes ATCC 25147 | 2 |
| Streptococcus agalactiae ATCC 13813 | 2 |
| Streptococcus group F ATCC 12392 | 2 |
| Streptococcus group G ATCC 12394 | 2 |
| Streptococcus group B ATCC 12386 | 2 |
| Streptococcus group C ATCC 12388 | 2 |

Biological Test Example-2

Oral (15 mg/kg p.o) pharmacokinetic studies were done in dog. Blood samples were collected at time points of 0, 0.08 (not for oral), 0.25, 0.50, 1.0, 1.5, 2.0, 3.0, 4.0, 5.0, 6.0, 8.0, 10.0, 12.0 and 24.0 h. To facilitate IV dosing and collection of blood samples, the dogs were implanted with cannula in cephalic vein. Serum obtained from blood samples was used for HPLC-based analysis.

Serum samples were extracted by solid phase extraction technique using Water's OASIS HLB cartridges. An HPLC-Diode array detection system was used for analysis. Prepared samples were chromatographed on a YMC-AM reversed phase column (150×4.6 mm ID; 5 µm) using an isocratic mobile phase acetate buffer (50 mmol ammonium acetate pH 6.6) acetonitrile, 66:34% v/v (for a representative compound of the invention) at a flow rate of 1 ml/min, measured at $\lambda_{max}$ 254 nm. Independently prepared analytical standards and quality control samples were analyzed with each set of unknown samples.

TABLE 2

Serum concentrations between 0-24 h.

| Time Point (hr) | Example-11 |
|---|---|
| 0.0 | 0.0 |
| 0.25 | 4.14 |
| 0.5 | 5.41 |
| 1.0 | 8.76 |

TABLE 2-continued

Serum concentrations between 0-24 h.

| Time Point (hr) | Example-11 |
|---|---|
| 2.0 | 11.42 |
| 3.0 | 10.97 |
| 4.0 | 10.37 |
| 5.0 | 8.81 |
| 6.0 | 7.28 ± 2.14 |
| 8.0 | 5.82 ± 1.58 |
| 10.0 | 4.50 ± 1.03 |
| 12.0 | 3.47 ± 1.25 |
| 24.0 | 2.19 ± 1.91 |

Result: The serum concentration up to 24 h is above MIC value, post dosing.

We claim:

1. A compound having the structure of Formula I:

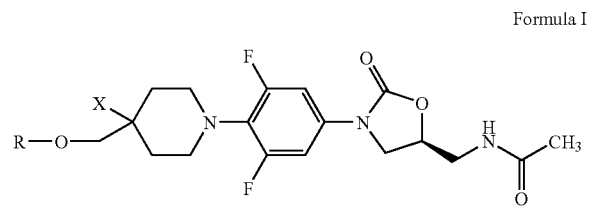

Formula I and its pharmaceutically acceptable salts, wherein
X is OH; and
R is $CH_3$.

2. A compound, which is (5S)—N-{3-[3,5-difluoro-4-(4-hydroxy-(4-methoxymethyl)-piperidin-1-yl)phenyl]-2-oxo-oxazolidin-5-ylmethyl}-acetamide.

3. A pharmaceutical composition comprising a therapeutically effective amount of a compound as defined in claim 1 or 2 optionally together with pharmaceutically acceptable carriers, excipients or diluents.

4. A method for treating bacterial infections in an animal or a human comprising administering to said animal or human, a therapeutically effective amount of a compound having the structure of Formula I:

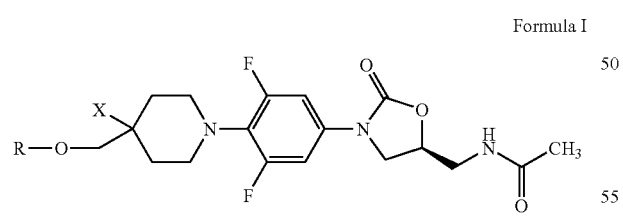

Formula I or a pharmaceutically acceptable salt, wherein
X is OH; and
R is $CH_3$.

5. The method according to claim 4, wherein the bacterial infections are caused by Gram-positive, Gram-negative bacteria, aerobic, anaerobic bacteria or atypical bacteria.

6. The method for treating bacterial infections in an animal or a human comprising administering to said animal or human, a pharmaceutical composition according to claim 3.

7. A process for preparing a compound of Formula I,

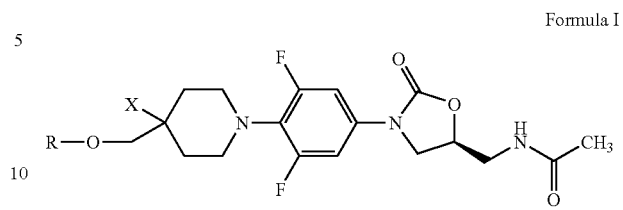

Formula I and its pharmaceutically acceptable salts, wherein
X is OH; and
R is $CH_3$;
the process comprising:

a) converting compound (4) into compound of Formula II;

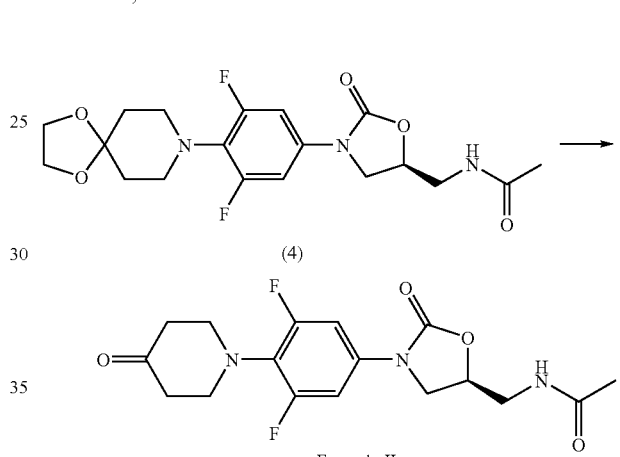

(4)

Formula II b) converting carbonyl of compound of Formula II into epoxide to form a compound of Formula III using a suitable reagent; and

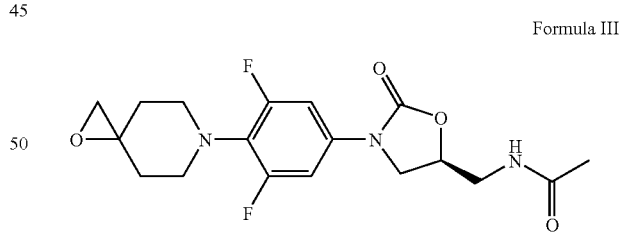

Formula III c) opening the epoxide of compound of Formula III to give a compound of Formula I

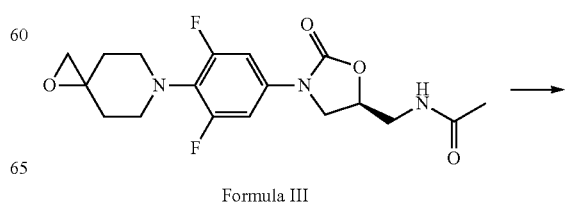

Formula III

-continued

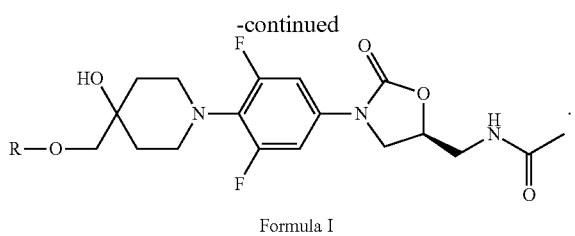

Formula I

8. The process of claim 7, wherein the conversion of the compound (4) into a compound of Formula II comprises the following steps in any suitable reaction order:
   a) hydrolyzing the ketal group to convert into carbonyl group;
   b) converting mesylate group into azide;
   c) reducing the azide to amine; and
   d) acetylating the amine to form acetamide.

9. The process of claim 7, wherein the suitable reagent is trimethyl oxosulfonium iodide or trimethyloxosulfonium chloride.

10. The process of claim 7, wherein the epoxide is opened using an alkoxide or an alcohol in presence of a base to give a compound of Formula I.

11. The process of claim 10, wherein the alkoxide is sodium methoxide.

12. The process of claim 10, wherein the alcohol is methanol, trifluoromethanol, difluoroethanol, trifluoroethanol, difluoropropanol or trifluoropropanol.

13. The process of claim 10, wherein the base is sodium carbonate, potassium carbonate, sodium tert-butoxide or potassium tert-butoxide.

* * * * *